United States Patent
Hwang et al.

(10) Patent No.: US 9,512,173 B2
(45) Date of Patent: Dec. 6, 2016

(54) METHOD FOR SEPARATING AND PURIFYING PROTEIN FROM PLANTS USING CELLULOSE AND CELLULOSE BINDING DOMAIN

(71) Applicant: BIOAPPLICATIONS INC., Gyeongsangbuk-do (KR)

(72) Inventors: Inhwan Hwang, Gyeongsangbuk-do (KR); Soo Hong Park, Gyeongsangbuk-do (KR); Yong Jik Lee, Gyeongsangbuk-do (KR); Eun Ju Sohn, Gyeongsangbuk-do (KR); Kyung Min Min, Daejeon (KR)

(73) Assignee: BIOAPPLICATIONS INC., Gyeongsang buk-do (KR)

( * ) Notice: Subject to any disclaimer, the term of this patent is extended or adjusted under 35 U.S.C. 154(b) by 0 days.

(21) Appl. No.: 14/433,762

(22) PCT Filed: Sep. 25, 2013

(86) PCT No.: PCT/KR2013/008599
§ 371 (c)(1),
(2) Date: Apr. 6, 2015

(87) PCT Pub. No.: WO2014/054865
PCT Pub. Date: Apr. 10, 2014

(65) Prior Publication Data
US 2015/0274772 A1    Oct. 1, 2015

(30) Foreign Application Priority Data
Oct. 5, 2012    (KR) .................. 10-2012-0110897

(51) Int. Cl.
  *C07K 1/32*    (2006.01)
  *C07K 1/22*    (2006.01)
  *C07K 14/005*    (2006.01)

(52) U.S. Cl.
  CPC . *C07K 1/32* (2013.01); *C07K 1/22* (2013.01); *C07K 14/005* (2013.01)

(58) Field of Classification Search
  None
  See application file for complete search history.

(56) References Cited

U.S. PATENT DOCUMENTS

| 4,058,411 A | 11/1977 | Bellamy et al. |
| 7,834,161 B2 * | 11/2010 | Mantyla .................. C07K 1/22 435/69.1 |

FOREIGN PATENT DOCUMENTS

| WO | 94/24158 A1 | 10/1994 |
| WO | 02/38746 A2 | 5/2002 |
| WO | 2005/023981 A2 | 3/2005 |
| WO | 2007/146944 A2 | 12/2007 |
| WO | 2010/131088 A1 | 11/2010 |

OTHER PUBLICATIONS

Hussack et al., "Purification of Plant-Derived Antibodies through Direct Immobilization of Affinity Ligands on Cellulose", J. Agric. Food Chem. 2010, 58, 3451-3459. DOI:10.1021/jf9040657.*
Boraston et al., "Binding Specificity and Thermodynamics of a Family 9 Carbohydrate-Binding Module from *Thermotoga maritima* Xylanase 10A", Biochemistry 2001, 40, 6240-6247.*
The extended European Search Report, seven pages, dated Feb. 5, 2016.
Novy et al., "New pET expression vectors generate fusion proteins with cellulose binding domains", InNovations, vol. 7, pp. 4-7, (1997).
Zhang et al., "Dissolution of Microcrystalline Cellulose in Phosphoric Acid—Molecular Changes and Kinetics", Molecules, vol. 14, pp. 5027-5041, (2009).

* cited by examiner

*Primary Examiner* — Suzanne M Noakes
(74) *Attorney, Agent, or Firm* — Vorys, Sater, Seymour & Pease LLP; Mih Suhn Koh

(57) ABSTRACT

The present invention relates to a method of isolating a protein containing a cellulose binding domain from plants using various structures of cellulose and/or variants thereof. According to the method of isolating a protein, as a high affinity cellulose binding domain is used, a high purity recombinant protein is rapidly and effectively isolated in large quantities at low cost, and thus can be applied in various industrial fields.

9 Claims, 4 Drawing Sheets

METHOD FOR SEPARATING AND PURIFYING PROTEIN FROM PLANTS USING CELLULOSE AND CELLULOSE BINDING DOMAIN

SEQUENCE LISTING

The Sequence Listing submitted in text format (.txt) filed on Apr. 23, 2015, named "Sequence_Listing.txt", created on Apr. 23, 2015, 2.24 KB, is incorporated herein by reference.

TECHNICAL FIELD

The present invention relates to a method of isolating a protein containing a cellulose binding domain using various structures of cellulose and/or variants thereof.

BACKGROUND ART

Cellulose is a basic component constituting a cell membrane and a xylem, and a type of an organic compound contained in a plant at approximately 30% or more. The cellulose is a polysaccharide with a chemical structure consisting of a plurality of D-glucose units linked by a β-1,4 glycoside bond, and a molecular weight of several tens of thousands to several hundreds of thousands in a natural state. The cellulose is a white odorless solid and insoluble in water, ethanol and ether, and has a considerably strong resistance to an alkali. However, the cellulose is hydrolyzed in an acid or cuprammonium solution, thereby producing a great quantity of cellobiose as an intermediate, and is finally converted into glucose. Since the cellulose is one of the most abundant natural resources in nature, many studies for utilizing it are progressing.

Meanwhile, cellulase that decomposes cellulose has a cellulose binding domain (CBD), and thus specifically binds to cellulose to effectively decompose it. There have been various attempts to produce a recombinant protein specifically binding to cellulose by binding such a cellulose binding domain to a target protein (Korean Patent No. 10-0618563). However, such attempts are limited to methods of producing a recombinant protein using a microorganism, and an example using plants has not been reported.

However, recently, since attention is focused on production of plant-derived recombinant proteins or vaccines, development of a method of producing a great quantity of recombinant proteins using plants, and rapidly isolating a high purity recombinant protein in large quantities at low cost is urgently needed.

DISCLOSURE

Technical Problem

The present invention is provided to solve conventional technical problems, and therefore it is directed to providing a method of isolating a protein containing a cellulose binding domain using various structures of cellulose and/or variants thereof to rapidly and simply isolate a protein expressed in plants in large quantities.

However, technical objects accomplished by the present invention are not limited to the above-described objects, and thus other objects should be clearly understood from the following descriptions by those of ordinary skill in the art.

Technical Solution

One aspect of the present invention provides a method of isolating a protein containing a cellulose binding domain, which includes:

(a) a protein binding step in which a plant extract containing proteins and cellulose are mixed;

(b) a washing step in which non-binding proteins are removed; and (c) an elution step in which the proteins binding to the cellulose are eluted.

In one embodiment of the present invention, the cellulose may be microcrystalline cellulose or amorphous cellulose.

In another embodiment of the present invention, the microcrystalline cellulose may be used 0.5 to 2 times the content of the plant extract.

In still another embodiment of the present invention, the amorphous cellulose may be used 0.1 to 0.5 times the content of the plant extract.

In yet another embodiment of the present invention, the amorphous cellulose may be produced by a method including: (a) producing amorphous cellulose by adding microcrystalline cellulose to 40 to 75% phosphoric acid and stirring the mixture; and (b) adding 500 mM to 1.5 M sodium carbonate ($Na_2CO_3$) to the amorphous cellulose.

In yet another embodiment of the present invention, the protein containing a cellulose binding domain may include an amino acid sequence of the cellulose binding domain represented by SEQ. ID. NO: 2.

In yet another embodiment of the present invention, in the protein binding step, a buffer containing 10 to 60 mM sodium acetate, 10 to 200 mM sodium chloride and 0.1 to 3 mM calcium chloride may be used.

In yet another embodiment of the present invention, in the washing step, a buffer containing 10 to 60 mM sodium acetate, 10 to 200 mM sodium chloride, 0.1 to 3 mM calcium chloride and 0.05 to 0.2% Triton X-100 may be used.

In yet another embodiment of the present invention, in the elution step, a buffer containing 10 to 60 mM Tris-HCl buffer with a pH of 7.5 to 10, 10 to 200 mM sodium chloride, 0.1 to 3 mM calcium chloride and 1 to 20% cellobiose may be used.

Advantageous Effects

According to a method of isolating a protein containing a cellulose binding domain of the present invention, since cellulose is used as a affinity matrix, compared to a conventional affinity matrix, the preparation for the method can be accomplished at low cost, and the content of a reagent used in the isolation according to a type of cellulose can be reduced. Therefore, a cost for isolating a protein can be considerably reduced, and a great quantity of protein can be isolated. In addition, as the cellulose binding domain having high affinity to cellulose is used, a high purity protein can be rapidly isolated from a total extract of a plant body in which various proteins are mixed by preventing non-specific binding of proteins, and a low concentration of protein can also be isolated.

MODES OF INVENTION

Figure 1:
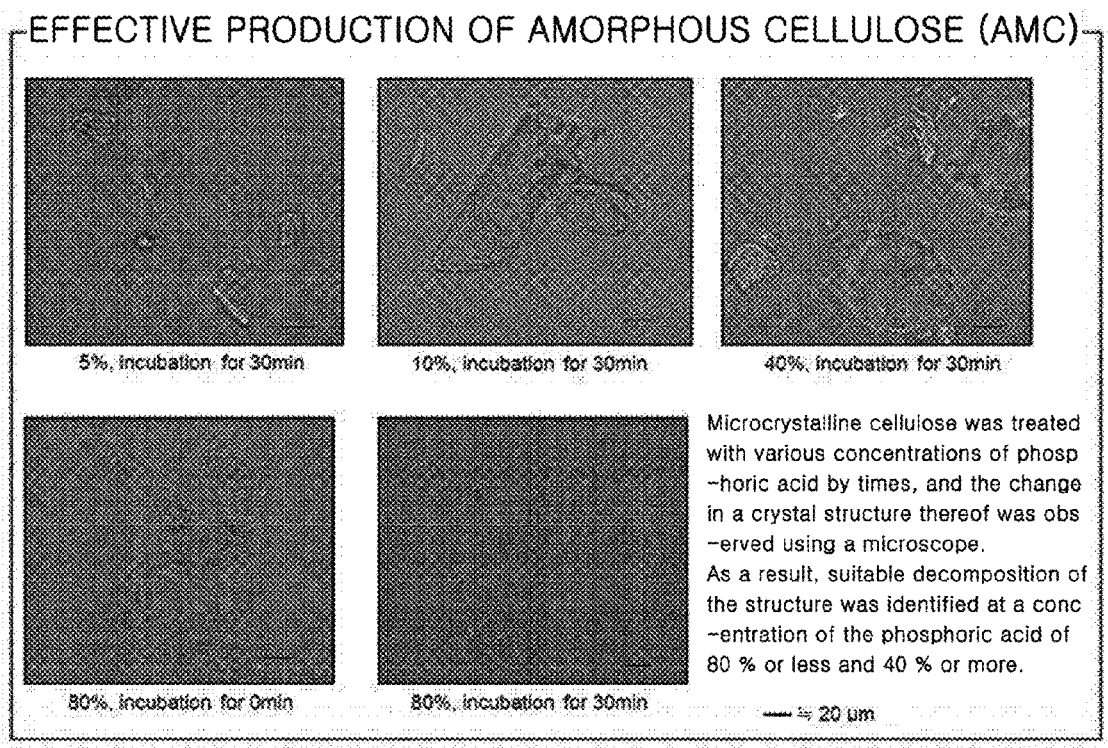
FIG. 1 is a diagram showing effective production of amorphous cellulose to be used in isolation and purification of a protein from a plant extract.

The present invention provides a method of isolating a protein containing a cellulose binding domain, the method including the following steps:

(a) a protein binding step in which a plant extract containing a protein and cellulose are mixed;

(b) a washing step in which non-binding proteins are removed; and (c) an elution step in which the proteins binding to the cellulose are eluted.

As a result of studying a method of rapidly isolating a great quantity of a high purity recombinant protein from a plant body at low cost, the inventors completed the present invention. That is, in one exemplary embodiment of the present invention, it was noted that a recombinant vector is manufactured by binding a cellulose binding domain (CBD) consisting of the base sequence of SEQ. ID. NO: 1 or the amino acid sequence of SEQ. ID. NO: 2 to the 3' end of a gene encoding a target protein, a transgenic plant body producing the target protein is manufactured using the recombinant vector, and the target protein is isolated using microcrystalline cellulose (MCC) and/or amorphous cellulose (AMC) (referred to Examples 1 to 3).

As described above, the inventors realized that the target protein can be easily eluted from a plant body in which the target protein containing a cellulose binding domain was expressed using cellulose.

Accordingly, the present invention may provide a method of isolating a protein containing a cellulose binding domain.

More particularly, in the present invention, the cellulose may be microcrystalline cellulose or amorphous cellulose. Here, the microcrystalline cellulose may be used at a content 0.5 to 2 times the content of a plant extract, and preferably, at the same content as the content of the plant extract. The amorphous cellulose may be used at a content 0.1 to 0.5 times the content of the plant extract, but the present invention is not limited thereto, and the content may be adjusted according to a condition, for example, a degree of expression of the target protein.

In addition, the amorphous cellulose may be produced by adding microcrystalline cellulose to 40 to 75% phosphoric acid and stirring the mixture, and adding 500 mM to 1.5 M sodium carbonate ($Na_2CO_3$) to the amorphous cellulose, but the present invention is not limited thereto.

In the present invention, the target protein containing the cellulose binding domain may be a recombinant protein consisting of an amino acid sequence of the cellulose binding domain represented by SEQ. ID. NO: 2 or a sequence exhibiting substantially the same activity as the amino acid sequence.

Here, the "substantially the same activity" means an activity of the cellulose binding domain, and may include an amino acid sequence variant which is functionally the same as an original one, but contains a substituted, deleted or added part.

In the method of isolating a protein containing a cellulose binding domain according to the present invention, the protein binding step may be performed using a buffer containing 10 to 60 mM sodium acetate (NaOAC), 10 to 200 mM sodium chloride (NaCl) and 0.1 to 3 mM calcium chloride ($CaCl_2$), and preferably, a buffer containing 50 mM sodium acetate, 50 mM sodium chloride, and 1 mM calcium chloride.

In addition, here, the washing step may be performed using a buffer containing 10 to 60 mM sodium acetate (NaOAC), 10 to 200 mM sodium chloride (NaCl), 0.1 to 3 mM calcium chloride ($CaCl_2$) and 0.05 to 0.2% Triton X-100, and preferably, a buffer containing 50 mM sodium acetate, 50 mM sodium chloride, 1 mM calcium chloride, and 0.1% Triton X-100.

In addition, here, the elution step may be performed using a buffer containing a 10 to 60 mM Tris-HCl buffer with a pH of 7.5 to 10, 10 to 200 mM sodium chloride (NaCl), 0.1 to 3 mM calcium chloride ($CaCl_2$) and 1 to 20% cellobiose, and preferably, a buffer containing a 50 mM Tris-HCl buffer with a pH of 8.8, 50 mM sodium chloride, 1 mM calcium chloride and 1% cellobiose.

The term "target protein (or protein)" used herein refers to a protein to be produced by a genetic engineering method according to the present invention, but the present invention is not particularly limited to one protein. The target protein may include proteins which can be used in a commercial application and is necessary to be produced in large quantities.

Hereinafter, to help in understanding the present invention, exemplary embodiments will be described. However, the exemplary embodiments are simply provided to more easily understand the present invention, but the scope of the present invention is not limited to the following exemplary embodiments.

EXAMPLES

Example 1

Manufacture of Transgenic Plant Body

To manufacture a transgenic plant body expressing a target protein, a recombinant vector was manufactured by binding a cellulose binding domain (CBD) consisting of a base sequence of SEQ. ID. NO: 1 or an amino acid sequence of SEQ. ID. NO: 2 to the 3' end of a gene encoding a target protein (porcine cholera virus glycoprotein gp55) to insert the gene into a vector for expressing plants, pCAMBIA 1300, and the vector was transformed into *Agrobacterium tumefaciens* LBA-4404 strains. In addition, transgenic plant bodies producing the target protein were manufactured by transforming *Arabidopsis thaliana* ecotype Col-1 using the *Agrobacterium* strain, and the transgenic plant body producing the target gene to which the cellulose binding domain was stably bound was screened for.

Example 2

Isolation of Protein Using Microcrystalline Cellulose

To isolate the protein using microcrystalline cellulose (MCC), hydration was performed by adding 2.5 g of microcrystalline cellulose to distilled water, the hydrated microcrystalline cellulose was charged to a column to remove the water. In addition, the transgenic plant body manufactured by the method of Example 1 was planted in soil and grown for approximately 3 weeks, thereby obtaining the plant body except roots, and then 2.5 g of the plant body, which had the same amount as that of the microcrystalline cellulose, was put into a mortar and pulverized using liquid nitrogen. After the pulverized plant body was transferred into a new tube, and an extraction buffer was added and mixed to have a concentration of 5 ml per g of the plant body, a 0.5× protease inhibitor was added, and then mixed by vortexing. In addition, the plant body was homogenized through ultra sonication for 10 minutes, and a plant homogenate from which debris was removed through miracloth was obtained. The obtained plant homogenate was added to the column containing the microcrystalline cellulose, the microcrystalline cellulose was mixed with the plant homogenate such that a cellulose binding domain bound to the microcrystalline cellulose, and the plant homogenate contained in the column was added at a rate of 100 μl/min. Afterward, a first washing was performed using 15 ml of a washing buffer [50 mM NaOAC (pH 5.2), 50 mM NaCl, 1 mM $CaCl_2$] with 0.1% Triton X-100, and a second washing was performed using a washing buffer without Triton X-100. Protein isolation was performed by adding an elution buffer [5 0 mM Tris-HCl (pH 8.8), 50 mM NaCl, 1 mM $CaCl_2$, 1% cellobiose] at a rate of 200 μl/min. While isolating a protein, it was careful not to dry microcrystalline cellulose. The isolated protein was identified by Coomassie blue staining and western blotting using an antibody binding to the cellulose binding domain. The results are shown in FIG. 2.

Figure 2:
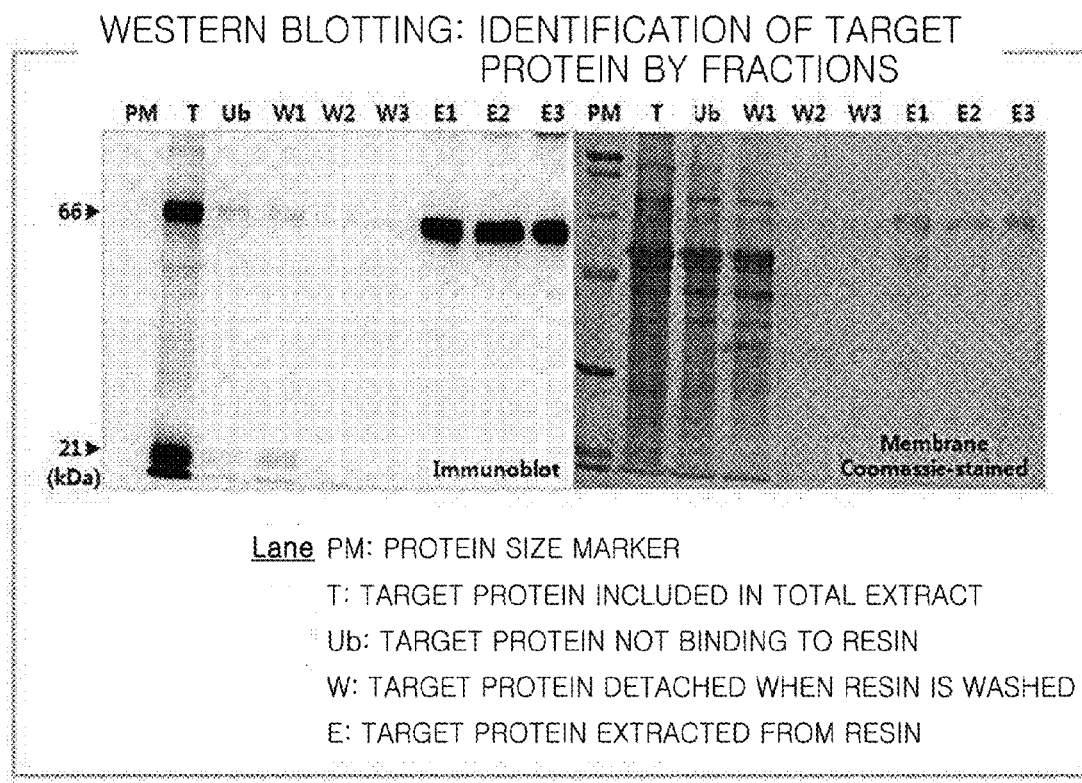
FIG. 2 shows a western blotting result for a protein isolated using microcrystalline cellulose.

As shown in FIG. 2, it was determined that a protein with a size of the target protein, 660 kDa, to which the cellulose binding domain was bound, was isolated. In addition, it was determined that, in the washing steps (W1 to W3), proteins binding to cellulose were rarely eluted, but in the elution steps (E1 to E3), proteins were still isolated at the third elution.

Example 3

Isolation of Protein Using Amorphous Cellulose

<3-1> Production of Amorphous Cellulose

To isolate a protein using amorphous cellulose (AMC), a method of changing cellulose into a crystalline type by treating microcrystalline cellulose with phosphoric acid at 4° C. was used. First, amorphous cellulose was manufactured by reacting the microcrystalline cellulose with 5, 10, 40 and 80% phosphoric acids, each reaction performed for 30 minutes, and the manufactured amorphous cellulose was observed using a microscope. The result is shown in FIG. 1.

As shown in FIG. 1, it can be determined that in amorphous cellulose produced by treatment with 80% phosphoric acid, right after treating the phosphoric acid, a crystal structure disappeared, and it can also be determined that, when the amorphous cellulose filled a column, and distilled water was added, the distilled water did not permeate the amorphous cellulose. It can also be determined that in amorphous cellulose treated with 40% phosphoric acid for 30 minutes, a crystal structure disappeared. According to the above results, it was determined that, when 40% or more, or 80% or more phosphoric acid was used as a treatment, suitable amorphous cellulose was manufactured and used in isolation of a protein. Based on this, in the following example, amorphous cellulose was manufactured by adjusting a final concentration of phosphoric acid to 60%.

2 g of microcrystalline cellulose was added to 6 ml of distilled water, and stirred for 2 to 3 minutes, and phosphoric acid was gradually added to have a final concentration of 60% and stirred to completely mix, and additionally stirred for 30 minutes. The stirred solution was put into two different tubes, 20 ml of distilled water was added to each tube to mix with the solution, and the resulting solution was centrifuged (14,000 rpm, 4° C., 10 minutes) to remove a supernatant. A process including adding 2 ml of 1 M $Na_2CO_3$ to crystallized cellulose, mixing them through vortexing, and centrifuging (14,000 rpm, 4° C., 10 minutes) the resulting mixture again to remove a supernatant was performed twice to completely remove a supernatant, and 1 ml of 1 M Na2CO3 and 20 ml of distilled water were added to the cellulose and mixed through vortexing. In addition, distilled water was added again to adjust an amount of the distilled water to have a final volume of 200 ml, and stored at 4° C. It was determined that the amorphous cellulose produced by the method had a stable pH of 6 to 9.

<3-2> Isolation of Protein Using Amorphous Cellulose

Figure 3:
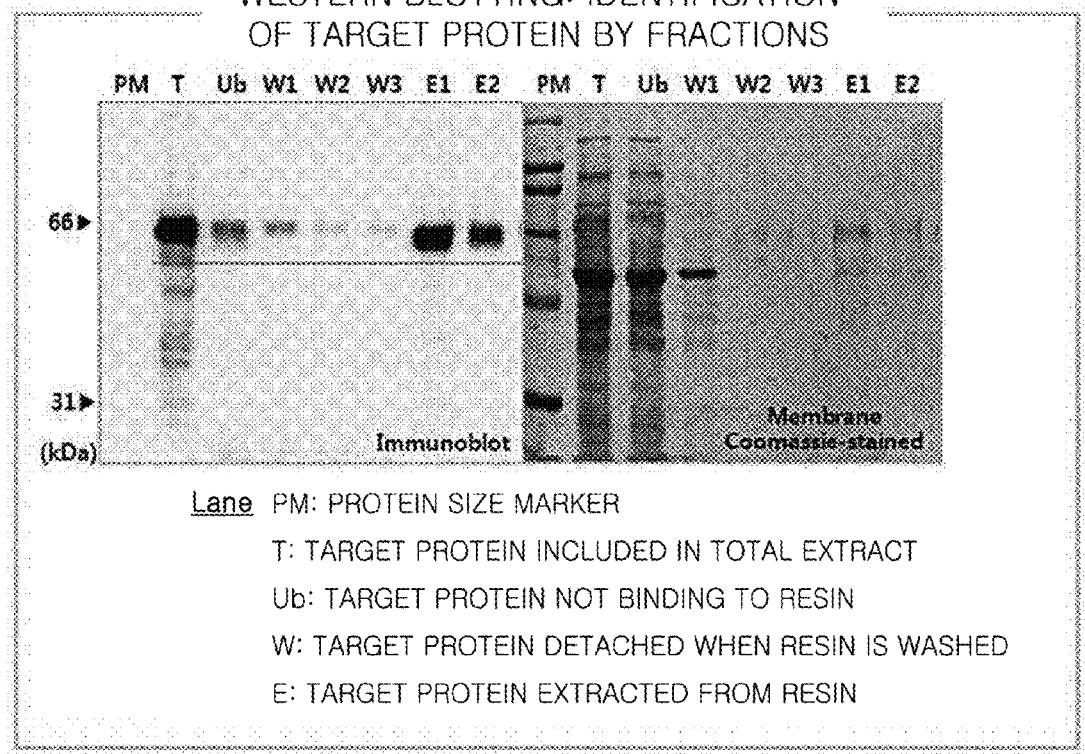
FIG. 3 shows a western blotting result for a protein isolated using amorphous cellulose.

To isolate a protein using amorphous cellulose (AMC) produced by the method described in Example 3-1, a column was filled with 0.5 g (50 ml) of amorphous cellulose. In addition, a plant homogenate prepared by the same method as described in Example 2 was added to the column filled with the amorphous cellulose and well mixed, and added at a rate of 100 μl/min. Afterward, 4 ml of a washing buffer [50 mM NaOAC (pH 5.2), 50 mM NaCl, 1 mM $CaCl_2$] with 0.1% Triton X-100 was added at a rate of 1 ml/min to perform a first washing, and a second washing was performed by adding a washing buffer without Triton X-100. In addition, a protein was isolated by adding an elution buffer [50 mM Tris-HCl (pH 8.8), 50 mM NaCl, 1 mM $CaCl_2$ 1% cellobiose] at a rate of 200 μl/min. In the process of isolating a protein, it was careful not to dry the amorphous cellulose. The isolated protein was identified by western blotting using an antibody binding to a cellulose-binding domain. The result is shown in FIG. 3. In addition, a pattern of the isolated protein was identified on SDS-page through Coomassie blue staining. The result is shown in FIG. 4.

Figure 4:
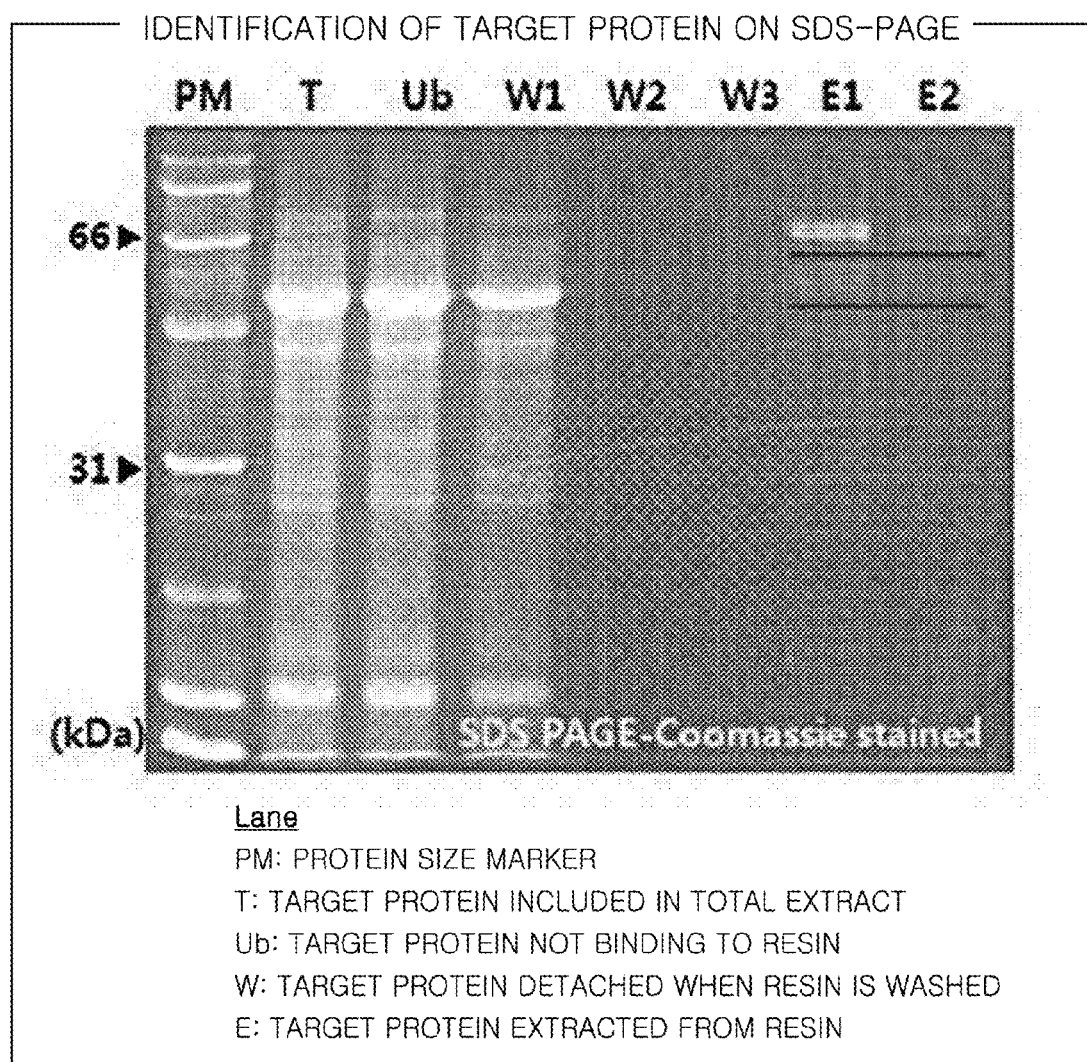
FIG. 4 shows the protein isolated using amorphous cellulose, which is identified on SDS-page through Coomassie blue staining.

As shown in FIGS. 3 and 4, it was determined that a protein with a size of a target protein, 66 kDa, to which a cellulose-binding domain was bound, was isolated, like the result as shown when the protein was isolated using microcrystalline cellulose. In addition, in the washing steps (W1 to W3), proteins binding to cellulose were rarely eluted, and in the elution steps (E1 and E2), a great quantity of proteins were isolated in the first elution, and the amount of eluted proteins was decreased from the second elution. According to the result, it can be determined that an elution time was reduced when amorphous cellulose was used.

Therefore, according to the method of isolating a protein using cellulose of the present invention, even when amorphous cellulose was used, the amount of a protein was almost the same as that when microcrystalline cellulose was used, and the amounts of a washing buffer and an elution buffer were decreased by ⅕ using amorphous cellulose in a volume approximately ⅕ smaller than a conventionally used amount, and finally, the time for isolating a protein was reduced by ⅕. It means that, when a great amount of proteins are isolated, due to a decrease in the number of samples used herein and a decreased time for isolation, working efficiency can be maximized.

The above description is to exemplify the present invention, and it would be understood by those of ordinary skill in the art that the present invention can be easily modified in different types without changing a technical spirit or essential characteristics of the present invention. Therefore, it should be understood that the above-described examples are exemplary in all aspects, but not limited.

According to a method of isolating a protein of the present invention, a great quantity of a high purity recombinant protein can be rapidly and effectively isolated from a plant body at low cost, and thus can be applied in various industrial fields.

The invention claimed is:

1. A method of isolating a protein containing a cellulose binding domain from a plant, comprising:
 (a) a protein binding step in which a plant extract containing the protein and other proteins and a cellulose are mixed;
 (b) a washing step in which non-binding proteins are removed; and
 (c) an elution step in which the proteins binding to the cellulose are eluted,
wherein the cellulose binding domain consists of the amino acid sequence of SEQ ID NO: 2.

2. The method according to claim 1, wherein the cellulose is a microcrystalline cellulose or amorphous cellulose.

3. The method according to claim 2, wherein the microcrystalline cellulose is used in an amount of 0.5 to 2 times the amount of the plant extract.

4. The method according to claim 2, wherein the amorphous cellulose is used in an amount of 0.1 to 0.5 times the amount of the plant extract.

5. The method according to claim 2, wherein the amorphous cellulose is produced by a method comprising:
   (a) producing amorphous cellulose by adding microcrystalline cellulose to 40 to 75% phosphoric acid and stirring the mixture; and
   (b) adding 500 mM to 1.5 M sodium carbonate ($Na_2CO_3$) to the amorphous cellulose.

6. The method according to claim 1, wherein the protein binding step is performed using a buffer containing 10 to 60 mM sodium acetate, 10 to 200 mM sodium chloride, and 0.1 to 3 mM calcium chloride.

7. The method according to claim 1, wherein the washing step is performed using a buffer containing 10 to 60 mM sodium acetate, 10 to 200 mM sodium chloride, 0.1 to 3 mM calcium chloride, and 0.05 to 0.2% Triton X-100.

8. The method according to claim 1, wherein the elution step is performed using a buffer containing a 10 to 60 mM Tris-HCl buffer with a pH of 7.5 to 10, 10 to 200 mM sodium chloride (NaCl), 0.1 to 3 mM calcium chloride ($CaCl_2$) and 1 to 20% cellobiose.

9. The method according to claim 1, wherein the protein binding is performed with a buffer containing 10 to 60 mM sodium acetate, 10 to 200 mM sodium chloride, and 0.1 to 3 mM calcium chloride; the washing is performed with a buffer containing 10 to 60 mM sodium acetate, 10 to 200 mM sodium chloride, 0.1 to 3 mM calcium chloride, and 0.05 to 0.2% Triton X-100; and the elution is performed with a buffer containing a 10 to 60 mM Tris-HCl buffer with a pH of 7.5 to 10, 10 to 200 mM sodium chloride (NaCl), 0.1 to 3 mM calcium chloride ($CaCl_2$) and 1 to 20% cellobiose.

* * * * *

SEQUENCE LISTING

<160> NUMBER OF SEQ ID NOS: 2

<210> SEQ ID NO 1
<211> LENGTH: 426
<212> TYPE: DNA
<213> ORGANISM: Artificial Sequence
<220> FEATURE:
<223> OTHER INFORMATION: Clostridium stercorarium - CBD base seq.

<400> SEQUENCE: 1

| | | |
|---|---|---|
| cgaagttcac cagtgcctgc acctggtgat aacacaagag acgcatattc tatcattcag | 60 | |
| gccgaggatt atgacagcag ttatggtccc aaccttcaaa tctttagctt accaggtggt | 120 | |
| ggcagcgcca ttggctatat tgaaaatggt tattccacta cctataaaaa tattgatttt | 180 | |
| ggtgacggcg caacgtccgt aacagcaaga gtagctaccc agaatgctac taccattcag | 240 | |
| gtaagattgg gaagtccatc gggtacatta cttggaacaa tttacgtggg gtccacagga | 300 | |
| agctttgata cttataggga tgtatccgct accattagta atactgcggg tgtaaaagat | 360 | |
| attgttcttg tattctcagg tcctgttaat gttgactggt ttgtattctc aaaatcagga | 420 | |
| acttct | 426 | |

<210> SEQ ID NO 2
<211> LENGTH: 142
<212> TYPE: PRT
<213> ORGANISM: Artificial Sequence
<220> FEATURE:
<223> OTHER INFORMATION: Clostridium stercorarium - CBD amino acid seq.

<400> SEQUENCE: 2

Arg Ser Ser Pro Val Pro Ala Pro Gly Asp Asn Thr Arg Asp Ala Tyr
1               5                   10                  15

Ser Ile Ile Gln Ala Glu Asp Tyr Asp Ser Ser Tyr Gly Pro Asn Leu
            20                  25                  30

Gln Ile Phe Ser Leu Pro Gly Gly Gly Ser Ala Ile Gly Tyr Ile Glu
        35                  40                  45

Asn Gly Tyr Ser Thr Thr Tyr Lys Asn Ile Asp Phe Gly Asp Gly Ala
    50                  55                  60

Thr Ser Val Thr Ala Arg Val Ala Thr Gln Asn Ala Thr Thr Ile Gln
65                  70                  75                  80

Val Arg Leu Gly Ser Pro Ser Gly Thr Leu Leu Gly Thr Ile Tyr Val
                85                  90                  95

Gly Ser Thr Gly Ser Phe Asp Thr Tyr Arg Asp Val Ser Ala Thr Ile
            100                 105                 110

Ser Asn Thr Ala Gly Val Lys Asp Ile Val Leu Val Phe Ser Gly Pro
        115                 120                 125

Val Asn Val Asp Trp Phe Val Phe Ser Lys Ser Gly Thr Ser
    130                 135                 140